United States Patent
Christensen et al.

(10) Patent No.: US 8,465,944 B2
(45) Date of Patent: Jun. 18, 2013

(54) HORIZONTAL ANTIGEN RETRIEVAL

(75) Inventors: Nanna K. Christensen, Lynge (DK); Lars Winther, Smorun (DK)

(73) Assignee: Dako Instrumec AS, Oslow (NO)

( * ) Notice: Subject to any disclaimer, the term of this patent is extended or adjusted under 35 U.S.C. 154(b) by 618 days.

(21) Appl. No.: 12/526,323

(22) PCT Filed: Feb. 11, 2008

(86) PCT No.: PCT/DK2008/000066
§ 371 (c)(1),
(2), (4) Date: Feb. 16, 2010

(87) PCT Pub. No.: WO2008/095501
PCT Pub. Date: Aug. 14, 2008

(65) Prior Publication Data
US 2010/0136612 A1    Jun. 3, 2010

Related U.S. Application Data

(60) Provisional application No. 60/900,471, filed on Feb. 9, 2007.

(51) Int. Cl.
*G01N 1/28* (2006.01)
*G01N 1/44* (2006.01)
*G01N 1/30* (2006.01)
*G01N 33/48* (2006.01)

(52) U.S. Cl.
USPC .............. 435/40.52; 435/40.5; 435/40.51

(58) Field of Classification Search
USPC .......................... 435/40.5, 40.52
See application file for complete search history.

(56) References Cited

U.S. PATENT DOCUMENTS

| | | | | |
|---|---|---|---|---|
| 7,867,443 B2 * | 1/2011 | Key et al. | ............ | 422/64 |
| 2004/0029184 A1 | 2/2004 | Gourevitch | | |
| 2005/0123943 A1 * | 6/2005 | Cao et al. | ............ | 435/6 |

FOREIGN PATENT DOCUMENTS

| WO | WO 2006/007841 A2 | 1/2006 |
|---|---|---|
| WO | WO 2006/066039 A2 | 6/2006 |

OTHER PUBLICATIONS

Editor: Hayat "Factors Affecting Antigen Retrieval" Chapter 4, 2002, in Microscopy, Immunohistochemistry and Antigen Retrieval, New York, 71-93.*
DOW Ethylene Glycols, Dow Ethylene Glycols, 2012, available at www.dow.com/ethyleneglycol/about/properties.htm.*
DOW Propylene Glycol, Dow Propylene glycol: Propylene Glycol USP/EP, 2012, available at www.dow.com/propyleneglycol/products/pg_uspep.htm.*
Optim Synthetic Glycerine—Vapor Pressure and Boiling point, Optim Synthetic Glycerine—Vapor Pressure and Boiling point, 2012, available at www.dow.com/safechem/optim/optim-advantage/physical-properties/vapor.htm.*
Beebe, Kerry "Glycerin Antigen Retrieval," Microscopy Today, 1999, Issue 9 (Nov.), p. 30-31.
International Search Report for International Application No. PCT/DK2008/000066. dated Jun. 16, 2008.

* cited by examiner

*Primary Examiner* — Jon P Weber
*Assistant Examiner* — Charles Zoltan Constantine
(74) *Attorney, Agent, or Firm* — Finnegan, Henderson, Farabow, Garrett & Dunner, LLP

(57) ABSTRACT

The present invention relates to a method for enhancing immunoreactivity of a tissue or cell sample fixed in a fixing medium, a target retrieval composition and its use. The method comprises providing a carrier in a horizontal position, said carrier having thereon a tissue or cell sample, said tissue or cell sample being on top of the carrier; contacting substantially the tissue or cell sample side of the carrier with a buffered target retrieval solution, wherein the target retrieval solution remains otherwise exposed to the environment; heating the tissue or cell sample and the target retrieval solution to a temperature above 100° C. The invention furthermore concerns the automated immunohistochemical staining of said samples, in particular the reactivation of antigens masked by fixation.

27 Claims, No Drawings

HORIZONTAL ANTIGEN RETRIEVAL

This is a U.S. National Phase Application (under 35 U.S.C. §371) based on PCT/DK2008/000066, filed 11 Feb. 2008, which claims priority to U.S. Provisional Patent Application No. 60/900,471, filed 9 Feb. 2007, all of which are incorporated herein by reference in their entireties.

FIELD OF THE INVENTION

The present invention relates to a method for enhancing immunoreactivity of a tissue or cell sample fixed in a fixing medium, a target retrieval composition and its use. The invention furthermore concerns the automated immunohistochemical staining of said samples, in particular the reactivation of antigens masked by fixation.

BACKGROUND

Due to the introduction of specialized therapies for specific types of cancer, the importance of immunohistochemical staining for diagnosing cancers is increasing. Furthermore, the increasing demand for high throughput in pathology laboratories in combination with the importance of avoiding any procedural errors has emphasized the need for automation of the immunohistochemical procedures.

The majority of tissue obtained from clinical specimens is fixed in a cross-linking fixative such as formaldehyde. This procedure stops the natural degradation of the tissue and thus retains the morphology intact for many years. The fixation forms cross-links between reactive amino acids in the proteins of the tissue in the form of methylene bridges and a poly-oxy-methylene network, which prevents the elution of soluble proteins and retains the molecules in a spatial arrangement that closely resembles the living tissue. Subsequently, the tissue-sample is dehydrated and embedded in an embedding media, predominantly paraffin wax, which allows the tissue to be cut in sections of as little as 2 μm.

The fixation however causes some loss of antigenicity. The modifications introduced in the proteins either chemically changes the epitopes recognized by the antibodies or physically prevent access to the epitopes. Many antigen retrieval or target retrieval methods have been developed to restore the antigenicity of the tissue, and most fall in one of two groups.

One traditional method comprises treating the tissue with a proteolytic enzyme, which opens up the tissue to allow the antibodies access to the antigens. For some specific antibodies, this method is the preferred antigen retrieval procedure, but it suffers from some limitations. Since the proteolytic enzymes degrade the tissue-proteins, there is a significant risk of destroying the specific epitope in the protein that is recognized by the antibody, thus the antigenicity may be lost rather than being restored. Furthermore, prolonged proteolytic treatment may cause the proteins to loose their three-dimensional structure, which is also significant for antibody-antigen recognition. These factors obviously necessitate close control with incubation times, however the required incubation time is very dependant on the activity of the enzyme.

During storage, the enzymes will slowly degrade themselves, particularly if the storage temperature is higher than recommended, and thus the activity of the enzyme-solution may vary greatly with time. This means that the optimal incubation time changes with the age of the enzyme-solution and ideally it should be adjusted accordingly.

Another factor that affects the efficiency of proteolytic target retrieval is the length of fixation of the tissue. The degree of cross-linking in the tissue increases with the fixation time and thus tissue that has been fixed for 72 hours will need longer proteolytic treatment than one that has been fixed for 24 hours. Frequently, however the information concerning fixation time is not available, in which case it is not possible to make the corresponding adjustment in enzyme incubation time.

A fundamentally different method comprises of boiling the tissue in an aqueous solution also known as heat induced antigen retrieval (HIAR). This pre-treatment method is not as dependent on fixation time as the enzymatic pre-treatment, and is more widely used. The high temperature accelerates hydrolysis of the aldehyde-induced modifications and the aldehyde released is diluted in the water, thus preventing it from reacting with the proteins again.

In conventional HIAR, typical boiling times are between 20 and 40 minutes at 95-99° C., dependent on the antigen, to which is added a cooling time of approximately 20 minutes before the slides can be removed safely without any risk of drying out the tissue. When the jar with the cold target retrieval solution is placed in a pre-heated water bath it will take 20 to 30 minutes before it reaches 95-99° C., which has to be added to the total procedure time. Using a microwave oven can reduce this heating step to 2-3 minutes as described in U.S. Pat. No. 5,244,787, (herein incorporated by reference) however the boiling and cooling times are unchanged, and thus the total procedure still amounts to 45 to 60 minutes. Heating the slides and target retrieval solution in a pressure cooker or similar pressurized device can reduce the boiling time. Here the tissue can be boiled at temperatures above 100° C. This is of particular importance at high altitudes, where the boiling point of aqueous solutions is lowered compared to sea level. In spite of the relatively short boiling time, the entire HIAR protocol is similar in length to the non-pressurised protocol, since cooling the liquid to a temperature where the pressure cooker can be opened safely is very time-consuming.

In addition to pure distilled water, many reagents are used routinely for antigen retrieval including Tris, Urea, EDTA, Citrate and saline buffers. Furthermore many solutions contain detergents, the selection comprising both ionic and non-ionic surfactants. In spite of the extensive research in the area of staining enhancement, no universal method or reagent has been identified that works with all subsequent immunohistochemical or immunocytochemical procedures.

Previous reports describe the use of glycerol for antigen retrieval purposes. Beebe (Beebe, K., Microscopy Today, 1999, Iss 9 (November), 30-31) has reported using 80% glycerol in a conventional submerging antigen retrieval method.

While traditional heat induced antigen retrieval restores tissue antigenicity for a wide variety of antibodies it has serious drawbacks when it comes to automation of the procedure. The use of near-boiling buffers in a tank is difficult to incorporate into an immunohistochemistry staining-instrument. Pumping buffer in and out of the tank and heating the buffer-solution is time-consuming and the energy-consumption associated with boiling the tissue is very high. Water-evaporation from the buffer-solution is high, and additional buffer must be added during the incubation-time. Furthermore, the steam can cause burns on the operators and it will condense in other parts of the instrument, where it may jeopardize the electronic circuits of the instrument.

Altogether, these processes significantly add to the complexity of a staining-instrument, and such factors obviously affect the expenses for the instrument.

Ventana Medical Systems have on their Benchmark® instrument a horizontal target retrieval procedure, where the aqueous buffer on the glass-slide is covered by an oil, the so called Liquid Coverslip™, to reduce evaporation during heating. Furthermore, the humidity inside the instrument is kept at near 100%.

Another example of an instrument that does antigen retrieval as well as staining is the Bond-Max® from Vision Biosystems. They use a cover-tile that is placed over the slide.

Both of the instruments mentioned above have the problem that any liquid will evaporate relatively quickly at a temperature near its boiling temperature and both instruments require the use of a cover over the sample.

SUMMARY OF THE INVENTION

There are several problems inherent in the target retrieval methods described above. Enzymatic target retrieval is very dependent on the condition of the tissue, the stability of the enzymes and furthermore only works with some antibodies. Traditional HIAR is a long procedure, which is very energy consuming and difficult to automate due to evaporation from the target retrieval solution.

In order to solve the problems inherent in the prior art, we propose a horizontal target retrieval method based primarily on organic solvents with boiling points higher than the boiling point of water. Said method is preferably automated. This will reduce the amount of target retrieval solution used per sample, and thus the amount of energy used for heating the sample with the solution and the time spent waiting for the solution to cool. Furthermore, the method of the invention eliminates the need for any type of covering or other means for enclosing the sample with the reagents to prevent evaporation.

According to one embodiment the invention relates to a method for enhancing immunoreactivity of a tissue or cell sample fixed in a fixing medium comprising:
 providing a carrier in a horizontal position, said carrier having thereon a tissue or cell sample, said tissue or cell sample being on top of the carrier,
 contacting substantially the tissue or cell sample side of the carrier with a buffered target retrieval solution, wherein the target retrieval solution remains otherwise exposed to the environment
 heating the tissue or cell sample and the target retrieval solution to a temperature above 100° C.

According to a further embodiment, the present invention relates to a method wherein more than one tissue or cell sample is placed on top of the carrier.

According to a further embodiment, the present invention relates to a method further comprising removing the embedding medium using any solvent capable of lowering the melting point of the embedding medium and/or dissolving said medium.

According to another embodiment, the present invention relates to a method, wherein the carrier is a glass slide, slide made of a polymer material, or a membrane.

According to another embodiment the present invention relates to a method, wherein the buffered target retrieval solution has minimum evaporation at between 100° C. and 150° C.

According to another embodiment, the present invention relates to a method wherein the target retrieval solution is heated to between 100° C. and 200° C.

A further embodiment relates to a method, wherein the target retrieval solution is heated to between 100-150° C.

According to another embodiment, the present invention relates to a method wherein the target retrieval solution is heated to between 105-130° C.

A further embodiment relates to a method, wherein the target retrieval solution is heated to 120° C.

According to yet another embodiment, the present invention relates to a method wherein the target retrieval solution comprises a solvent having a boiling point significantly higher than the boiling point of water.

According to yet another embodiment, the present invention relates to a method wherein the target retrieval solution comprises a solvent having a boiling point higher than the boiling point of water and lower than 199° C.

According to another embodiment the present invention relates to a method, wherein the solvent is selected from a group consisting of alcohols, glycols, ketones, esters, amides and nitriles or a mixture thereof.

According to yet another embodiment the present invention relates to a method, wherein the solvent is glycerol.

According to yet another embodiment the present invention relates to a method, wherein the solvent is propylene glycol or ethylene glycol.

According to one embodiment the present invention relates to a method, wherein the target retrieval solution further comprises of one or more reagents capable of breaking bonds formed during fixation of the biological sample.

An even further embodiment relates to a method wherein the target retrieval solution comprises more than 25% of the solvent.

According to another embodiment, the present invention relates to a target retrieval solution comprises between 40-80% of the solvent.

According to a further embodiment the invention relates to a method wherein the target retrieval solution comprises between 45-75% of the solvent.

According to one embodiment the method of one embodiment of the invention relates to a target retrieval solution comprising about 50% of the solvent.

According to one embodiment the method of one embodiment of the invention relates to a target retrieval solution comprising about 80% of the solvent.

According to one embodiment the method of one embodiment of the invention relates to a target retrieval solution comprising a mixture of two solvents.

According to one embodiment the method of one embodiment of the invention relates to a target retrieval solution comprising a mixture of propylene glycol and ethylene glycol.

According to yet another embodiment the present invention relates to a method, wherein the fixing medium is formaldehyde, Bouins solution or other commonly used cross-linking agents.

According to a further embodiment the present invention relates to a method, further comprising automation of one or more of the steps.

According to one embodiment the present invention relates to a method, further comprising the step of cooling the slide and the solution after the heating step. According to one embodiment, the cooling step is performed by actively cooling the tissue or cell sample.

According to another embodiment the present invention relates to a method, further comprising the step of removing the target retrieval solution from the surface of the carrier after the heating and/or cooling step(s).

A further embodiment of the invention relates to a method, wherein the target retrieval solution is removed from the surface of the carrier with a further solvent capable of mixing with the target retrieval solution According to one embodiment, the present invention relates to a method wherein the further solvent is an aqueous washing buffer or ethanol.

According to another embodiment the present invention relates to a method, wherein the removing of the target retrieval is performed at ambient or above ambient temperature.

According to another embodiment the present invention relates to a method, further comprising renewing or replacing the target retrieval solution one or more times during heating.

According to one embodiment the present invention relates to a method, further comprising the step of staining the tissue or cell sample with a probe.

According to another embodiment the present invention relates to an aqueous target retrieval solution, comprising 50% glycerol, a TRIS buffer (e.g. between 0.1 mM and 1M TRIS buffer) containing EDTA (e.g. between 0.01 mM and 100 mM EDTA).

According to another embodiment the present invention relates to a target retrieval solution, comprising 50% glycerol, 40% water and 10% TRIS buffer containing EDTA.

According to another embodiment the present invention relates to an aqueous target retrieval solution, comprising 50% glycerol, a Citrat buffer (e.g. between 0.01 mM and 1M Citrat buffer) containing a detergent (e.g. between 0.01% and 5% detergent).

According to another embodiment the present invention relates to a target retrieval solution, comprising 50% glycerol, 40% water and 10% Citrate buffer containing a detergent.

According to another embodiment the present invention relates to a target retrieval solution, comprising 55% propylene glycol, 25% ethylene glycol, 10% water and 10% TRIS buffer containing EDTA.

According to another embodiment the present invention relates to a target retrieval solution, comprising 55% propylene glycol, 25% ethylene glycol, 10% water and 10% Citrate buffer containing a detergent.

According to one embodiment the present invention relates to a target retrieval solution, having a surface tension and viscosity that is sufficiently high for the solution not to run off the surface of the slide during heating.

According to another embodiment the present invention relates to a target retrieval solution, wherein the viscosity is between 4 and 7 cP at between 20 and 25° C.

A further embodiment of the invention relates to a target retrieval solution, wherein the water content is between 1 and 75% (v/v) of the target retrieval solution, According to yet another embodiment the present invention relates to a target retrieval solution, wherein the TRIS has a concentration between 0.1 mM and 1M, preferably between 1 mM and 100 mM, more preferably 10 mM.

According to another embodiment the present invention relates to a target retrieval solution, wherein the EDTA may have a concentration between 0.01 mM and 100 mM, preferably between 0.1 mM and 10 mM, more preferably 1 mM.

A further embodiment relates to an antigen retrieval solution, wherein the pH of the target retrieval solution may be between 2 and 10, preferably between 6 and 10, more preferably between 8 and 9.

According to yet another embodiment the present invention relates to a target retrieval solution, wherein the Citrate has a concentration between 0.1 mM and 1M, preferably between 1 mM and 100 mM, more preferably 2.5 mM.

According to another embodiment the present invention relates to a target retrieval solution, wherein the detergent may have a concentration between 0.01% and 5%, preferably between 0.05% and 1%, more preferably 0.1%.

A further embodiment relates to a target retrieval solution, wherein the pH of the target retrieval solution may be between 2 and 10, preferably between 4 and 8, more preferably between 6 and 7.

According to a further embodiment the present invention relates to the use of a target retrieval solution comprising glycerol, water, and one or more of the following; a nucleophile, a buffer a chelator or a detergent for horizontal antigen target retrieval.

DETAILED DESCRIPTION

A carrier in the context of the present invention may be any platform that can act as a carrier for the biological sample, e.g. a slide. It should preferably be larger than the sample itself, i.e. supporting the whole sample. Such suitable platforms include, but are not limited to various kinds of support known to a person skilled in the art, e.g. glass or polymer slides. Membranes, films and gels can also be suitable carriers.

In the context of the present invention the term "on top" of the carrier is to be understood as a substantially flat surface of the carrier facing upwards when the carrier is placed in a horizontal position. A small volume of a solution can be placed on top of the carrier without running off the edges of the carrier. The top surface can for example be one of the primary sample surfaces of a slide.

A biological sample in the context of the present invention is a cell sample, preferably a tissue sample or a cytological sample. A sample, which is fixed by cross-linking agents prior to immunopathologic, immunohistochemical, immunofluorescent examination or in situ hybridization, may be used in a method of the invention. Such samples may be tissue samples, fluidic samples or even environmental samples such as water samples. The tissue samples are usually fixed by cross-linking agents or are e.g. mucous swabs. The tissue samples are preferably formaldehyde-fixed samples, but also samples fixed with PLP (Periodate/Lysine/Paraformaldehyde), paraformaldehyde, Boonfix I, Boonfix II, Myrsky fixative, Bouin's solution, glutaraldehyde, zinc formalins or other aldehydes or other bi-functional cross-linkers can suitably be subjected to a method of the invention.

The immunoreactivity of a biological sample depends on the ability of an antibody raised against a specific epitope present in the biological sample, to recognize said epitope in the context of the sample. The epitope may also be denoted as the target or the antigen and these terms are used interchangeably through this text. The term target may also describe a part of the tissue that is recognized by something other than an antibody, e.g. DNA or DNA-analogues such as PNA or LNA or a stain that binds to specific compartments in the tissue/cell.

As used herein, the term "probe" is to be understood as any molecule that is capable of recognizing a specific target in the tissue or cell sample. This includes, but is not limited to antibodies, labeled for direct visualization or unlabeled using a secondary antibody for visualization, a DNA-binding molecule such as DNA, PNA, LNA or molecules capable of intercalating between nucleobases in DNA. These probes may all be visualized either by fluorescent dyes or chromogens visible in bright field microscopy. The term "probe" may also include stains that bind to specific areas of the tissue or cell-compartments.

As used herein, the term "primary solvent" is to be understood as a solvent, which alone forms the major part of a mixture, and thereby is the most influential factor for raising the boiling point of the mixture. Depending on the solvent the major part can for example be at least 30%, at least 50%, at least 60%, at least 70%, at least 80% or at least 90%.

In the context of the present invention the term "ambient temperature" is to be understood as the same temperature as the surrounding environment.

As used herein, the term "exposed to the environment" is to be understood as being exposed to temperature and air surrounding in the near environment of the sample, in contrast to contacting the interface of the target retrieval solution with a further interface other than gas. Such a closed environment could for example be a cover slide, a liquid cover slip, a cover tile or other means for enclosing the target retrieval solution as much as possible.

The method of the present invention can also be said to comprise an unenclosed coverless carrier. The term "unenclosed coverless carrier" is to be understood as being a carrier in which the target retrieval solution is exposed to the ambient temperature and air, in contrast to a covered carrier or an enclosed carrier. One example of an unenclosed coverless carrier is a carrier such as a microscope slide, which during target retrieval:
- is not enclosed or substantially immersed in a diptank, well, pocket, vat, chamber, or any type of liquid container; and
- does not have any type of solid or liquid coverslip that covers the target retrieval solution.

Hence, the method of the invention would be a method for enhancing immunoreactivity of a tissue or cell sample fixed in a fixing medium comprising:
- providing an unenclosed coverless carrier in a horizontal position, said carrier having thereon a tissue or cell sample, said tissue or cell sample being on top of the carrier,
- contacting substantially the tissue or cell sample side of said carrier with a buffered target retrieval solution, wherein the carrier in contact with the buffered target retrieval solution remains unenclosed and coverless during target retrieval,
- heating the tissue or cell sample and the target retrieval solution to a temperature above 100° C.

Heat induced antigen retrieval (HIAR) is a hydrolysis of the modifications induced by formaldehyde fixation. This conventionally means submerging the slide with the biological sample in a container containing an aqueous buffer and boiling said buffer for 20-40 minutes. Such a procedure requires among other a large amount of target retrieval solution and, hence, high energy consumption to heat the solution.

The present invention provides a reliable, more economical and faster method for target retrieval. By performing the reactions horizontally, the volume consumption is reduced considerably and as the process time likewise is reduced the energy consumption and man-hours are reduced considerably as well. Furthermore, the horizontal approach simplifies the apparatus required to run the process, and minimizes the use of reaction tanks and avoids the implementation of a pressure device or a microwave device in the apparatus, which would add an unwanted high level of complexity to the instrument. The need for a cover slip of any sort or a cover tile during antigen retrieval is also eliminated.

The method of the present invention can be combined with an automated horizontal procedure for removal of the embedding medium. This is traditionally performed by submerging the slide in a series of solvents capable of dissolving the embedding medium and rehydrating the tissue or cell sample. The automated procedure can consists of placing the carrier containing the tissue or cell sample horizontally and contacting it with a solvent capable of dissolving the embedding medium followed by a washing step that removes both solvent and dissolved embedding medium as described in patent application PCT/DK2006/000660 herein incorporated by reference. Such a horizontal procedure for removal of embedding medium in combination with a horizontal target retrieval procedure will completely eliminate the need for reagent-filled jars during the pretreatment of the tissue or cell sample. It will reduce the amount of reagent used and thus the amount of waste created during pretreatment as well as providing a shorter and less labor-intensive procedure.

Another advantage of the invention is that the method does not require the use of any covering of the sample and target retrieval solution, e.g. to prevent evaporation. The method of the present invention is in an open environment, i.e. uncovered, open to the air. It does not require a cover slip, a chamber or clip-on means that are designed to secure minimum evaporation. The evaporation control of the present invention is included in the solution itself, i.e. the inclusion of a solvent having a high boiling point.

To illustrate the amount of manual labor involved in a traditional pre-treatment, the following example is of a manual pre-treatment procedure with conventional removal of embedding medium in jars and HIAR using dip tanks:
a) An embedded biological sample is placed on a slide.
b) The embedding media is removed by dipping the slide and sample in a series of solvents capable of dissolving the embedding media and rehydrating the sample as known to those skilled in the art. This procedure takes approximately 25 minutes.
c) Meanwhile, a jar containing the aqueous target retrieval solution is placed in a water bath and heated to 95-99° C. The heating typically takes about 20-30 minutes, for heating 400 mL of target retrieval solution.
d) The slide with the sample is placed in the hot target retrieval solution for 20 minutes.
e) The jar containing target retrieval solution and slide with sample is removed from the water bath and is allowed to cool for approximately 20 minutes.
f) After a brief rinsing in aqueous buffer, the sample is ready for immunohistochemical staining.

This can be summarized to just over 1 hours work, with two 20 minutes interruptions.

In contrast, the following is an example of horizontal pretreatment, including removal of embedding medium and target retrieval. Steps b)-e) can be fully automated:
a) An embedded biological sample is placed on a slide.
b) The embedding media is removed by contacting the slide and sample with solvents capable of dissolving the embedding media and rehydrating the sample as described above. The solvents are applied to the slide while placed in a horizontal position. This step takes about 8 minutes.
c) The slides are placed in a horizontal position and a target retrieval solution suitable for horizontal target retrieval is applied to the sample. Such a solution preferably contains one or more organic solvents.
d) The sample and target retrieval solution are heated to a temperature sufficient for breaking the bonds formed during fixation, for 5-20 minutes. During this time, the reagent may be changed one or more times if necessary.
e) The sample and target retrieval solution are allowed to cool for about 1 minute and the target retrieval solution is washed of.
f) After a brief rinsing in aqueous buffer, the sample is ready for immunohistochemical staining.

This can be summarized to approximately 30 minutes turnaround time. A fully automated process includes maximum 10 minutes of manual labor for loading the slides with the tissue or cell sample into the instrument and programming the run.

These examples display the advantages of a horizontal process, especially when automated. With both removal of the embedding media and target retrieval performed horizontally, the turn-around-time is reduced to approximately half the time used for the corresponding manual procedures. In addition, the automated procedure requires only 5-10 minutes manual labor for loading the carriers containing tissue or cell sample into an instrument and programming the run. The reduction in human contact reduces the risk of human error. If an error is done e.g. during the programming of the instrument, it can be easily traced in the run-log of the instrument.

In order to perform target retrieval automatically a horizontal approach where only the biological sample is covered by reagent is advantageous in relation to reagent consumption, energy consumption and time. The carrier is in a substantially horizontal position, at least in such a way that the sample is covered with enough amount of solution during the process. Horizontal is to be understood as being parallel to, in the plane of, or operating in a plane essentially parallel to the horizon or to a baseline.

The present invention solves the problem of evaporation of the target retrieval solution during the process. The problem is solved with the use of a target retrieval solution comprising a high-boiling solvent having a boiling point significantly higher than the temperature required to break a bond between the tissue or cell sample and the fixing medium and thereafter heating the tissue or cell sample in the method of the present invention and the target retrieval solution to a temperature below the boiling point of the solvent and higher than the temperature required to break the bond between the tissue or cell sample and the fixing medium.

This method is particularly useful in automated procedures performed in an apparatus.

Adding other solvents to the target retrieval solution may prevent the reagent from evaporating totally, but it also reduces the water-activity and thus the speed of the hydrolysis. Increasing the reaction time or the temperature can compensate for the reduction in reaction speed. However, as increasing the reaction time goes against the wish for reduced turn-around time, increasing the temperature is the preferred method for compensating for the reduced speed of hydrolysis. Increasing the temperature above 100° C. will accelerate the evaporation of water and other solvents with boiling points in that temperature range.

In the context of the present invention the solvent of the target retrieval solution preferably has a boiling point that is "significantly higher" than the temperature to which the tissue or cell sample and target retrieval solution are heated. This is to be understood as having a boiling point that is so high that the solvent has a very low vapor pressure at the temperature to which the target retrieval solution is heated and thus does not evaporate to any measurable degree during 5, 10 or 15 minutes at this temperature, i.e. preferably not more than 30% of the target retrieval solution will evaporate, more preferably not more than 20%, more preferably not more than 15%, more preferably not more than 10%, more preferably not more than 5%. The boiling point of the solvent should for example be at least 150° C., at least 200° C., at least 220° C. or at least 250° C. However, the boiling point of the solvent can also be significantly higher.

The solvent for the horizontal target retrieval solution should preferably fulfill one or more of the following criteria:
 be miscible with water, since water is an essential part of the reagent
 not affect the hydrolysis reaction
 have a boiling point that is significantly higher than the boiling point of water.
 not evaporate significantly in 10 minutes at temperatures between 100 and 150° C.
 preferably not cause damage to the biological sample at temperatures between 100 and 150° C., even in essentially 100% concentration. The morphology of biological tissue or cells should preferably remain intact.
 have a surface tension that is sufficiently high for it to form a "drop" on the slide.
 be relatively easily removed form the biological sample after target retrieval. Preferably, it can be washed off with distilled water or aqueous buffers.
 be non-hazardous.

Furthermore, it is advantageous if the solvent is hygroscopic, meaning that it retains water. This will slow the evaporation of water, even at temperatures above 100° C.

The primary solvent is preferably selected from the list consisting of alcohols, glycols, ketones, esters, amides or nitriles. One type of primary solvent that works well is a glycol The primary solvent can also be a mixture of one or more of the above.

Due to the high polarity of water, polar solvents are preferred. examples of polar solvents include alcohols, such as methanol, ethanol, propanol, butanol, isopropanol, tert-butanol and glycols such as ethylene glycol, glycerol and propylene glycol. Other polar solvents include acetone, methylethylketone, ethylacetate, acetonitrile, formamide, N,N-dimethylformamide, dimethylsulfoxide and N-methylpyrrolidone. Many of these solvents have the advantage of being completely miscible with water, which makes it possible to wash of remaining solvent with aqueous buffers. Preferred solvents are glycols such as ethylene glycol, glycerol and propylene glycol or formamide, N,N-dimethylformamide, dimethylsulfoxide and N-methylpyrrolidone.

The target retrieval solution preferably comprises more than 25% solvent, more preferably more than 35% of the target retrieval solution. A particularly useful target retrieval solution contains between 40 and 60% solvent, for example 50% solvent. These concentrations ensure that the biological sample is still completely covered even in case a large amount of water evaporates. If the solution does not cover the entire sample, it will dry out, and this has a detrimental effect on the immunohistochemical staining that follows. Besides contributing to the increased temperature-tolerance of the target retrieval solution, the solvent has the added effect of maintaining the concentration of buffer, chelator, nucleophile and/or detergent sufficiently low if essentially all the water has evaporated. This prevents any damage to the tissue caused by the increased concentration of these components. Alternatively, the increased osmotic pressure may cause the cells to collapse or otherwise change shape, which will reduce the diagnostic value of the biological sample.

The boiling point of the primary solvent is higher than the boiling point of water as otherwise it would evaporate during heating. According to another embodiment the boiling point of the primary solvent is higher than the boiling point of water and less than 199° C.

Having a boiling point of 290° C., and being hygroscopic, glycerol is a particularly effective primary solvent. The target retrieval solution may comprise one or a mixture of two or more solvents. The solvents may be chosen from, but are not limited to the examples presented above.

The target retrieval solution can preferably be heated to between 100 and 200° C., more preferably between 100 and 150° C., even more preferably between 105 and 130° C. without drying out the sample. At this temperature, the target retrieval solution should have a surface tension that is sufficiently high to prevent it from running off the slide/sample carrier. Furthermore, the target retrieval solution should have no damaging effect on the biological sample, even after complete evaporation of the water content.

Optimum target retrieval which allows good staining of the tissue or cell sample can however not be obtained by using solvents alone. The inclusion of a hydrolyzing agent, such as water, in the target retrieval solution is preferred since the desired reaction is a hydrolysis, where the hydrolyzing agent causes a partial reversal of the modifications induced by the fixative and thus restores the epitopes to a state that permits recognition by the antibodies. Furthermore, a buffered target retrieval solution is also preferred in order to stabilize the pH of the solution. Some epitopes can be effectively demasked at both low and high pH, but not at neutral pH. Others have an optimum for demasking only at high pH, and others have their optimum in the low to neutral pH-range. Therefore, it is preferred to control the pH of the solution and optimize it to the targets that are to be demasked.

Before target retrieval the tissue or cell sample is fixed in a fixing medium. The selection of appropriate solvents for the target retrieval solution is dependent on the fixing medium in order to give optimum effect and well known to a person skilled in the art. The fixing medium is preferably the traditionally used formaldehyde.

The target retrieval solution comprises one or more reagents capable of breaking bonds formed during fixation of the biological sample, aiding in such a reaction, protecting the tissue-proteins from unwanted reactions and/or removing any free fixative.

The method of the present invention is particularly suitable for the automation of target retrieval. There are several advantages to a horizontal procedure:
- reduced reagent consumption since reagent is added to the surface of the slide, directly onto the biological sample.
- heating of smaller amounts of reagent leads to reduced energy-consumption.
- reduction of the waiting-time during heating of reagents.
- reduction of the waiting-time during cooling of reagents.

The evaporation of the aqueous reagent and subsequent drying of the biological sample during an automated horizontal procedure, can be avoided by the method of the present invention, i.e. adding a high-boiling solvent that protects the sample, such as glycerol.

A fully automated procedure for target retrieval is described as follows:
1. the slide with the biological sample is placed horizontally in the instrument, with the biological sample on top of the slide. Preferably the slide is not heated before the target retrieval solution is added, since this would quickly dry out the tissue.
2. target retrieval solution is added to the slide, the solution should cover the entire biological sample. the slide should essentially be level, since the reagent may otherwise run off or result in an uneven covering of the sample.
3. the slide containing the biological sample and the reagent is heated to the required temperature, either by heating the platform on which the slide is placed or by lowering it onto a preheated plate.
4. the slide with the biological sample and reagent is maintained at the required temperature for a predetermined time. The time is based on when the temperature of solution on the slide reaches a plateau, i.e. becomes stable for a predetermined amount of time, This is dependent on the amount of reagent, the evaporation of water from the reagent as well as ambient temperature, and is usually about 5 minutes.
5. the slide with the biological sample and solution can be actively cooled before the solution is removed. This can be done by moving the slide away from the heating platform or by actively cooling the platform.
6. a) if at this point the target retrieval is complete the slide is cooled to a temperature close to ambient and washed with water or an aqueous buffer to remove any residue of the target retrieval solution. The temperature is preferably sufficiently low to avoid drying out the sample when the protecting solvent of the target retrieval solution is removed.
   b) if at this point the target retrieval is not complete, the majority of the used reagent is removed and new solution is added. This exchange of reagent does not necessarily have to take place at ambient temperature, since the residue of the used reagent will protect the sample from drying out until the new reagent is added. The procedure continues from step 2.

Adding new reagent is repeated until target retrieval is satisfactory for the specific target. This is determined separately for each target in question. After washing, the slide with the biological sample is ready for immunohistochemical staining.

Selected steps and even all the steps as describe in the automated process above can also be performed manually.

In some embodiments, the heating platform may include Peltier thermoelectric devices (TEDs), resistive heating devices, and various combinations thereof. Two or more Peltier TEDs may also be stacked or otherwise combined to provide rapid heating in a small area such as the area of a microscope slide. Peltier thermoelectric devices (TEDs) may also be driven using pulse width modulation (PWM) or similar modulated energy techniques to optimize the power supply requirements to drive the TEDs while at the same time matching the heating time profile desired. In other embodiments, Peltier thermoelectric devices (TEDs) may be combined with other heating devices such as resistive heating devices. In some embodiments, the polarity of the electric current applied to Peltier thermoelectric devices may be reversed so as to actively cool the heating platform and optimize the heating and cooling profile over time.

In some embodiments, prior to heat induced antigen retrieval, the sample on the slide may be baked to promote tissue adhesion to the slide. Baking may be for any desired time, for example 60° C. for 60 minutes or may vary depending upon tissue type and moisture content and intended antigen retrieval protocol. Horizontal heating platforms of some embodiments of the invention may be used to perform both the baking and HIAR functions. For example, Peltier thermoelectric devices (TEDs) or similar heating platforms may be used to bake the slides at a low temperature and then the same TEDs may be used to heat the slides to greater than 100° C. for antigen retrieval.

While some embodiments may include TEDs, the heating platform may be any horizontal heating device capable of controlling the temperature within +/−2° C. up to 150° C. If the reagent is added to and removed from the slide while placed on the heating platform, it should be capable of forced heating and cooling. The heating platform should be capable of increasing the surface temperature from ambient to 150° C. within 10 minutes and cool it down to ambient again within 10 minutes. Preferably, the platform can force the surface temperature from ambient to 130° C. within 5 minutes or shorter and from 130° C. to ambient within 5 minutes or shorter. If an exchange of reagents is required while the slide remains in contact with the heating platform, the temperature should be lowered to between 50 and 100° C., preferably between 60 and 80° C. The heating platform should be capable of forcing the surface temperature from 150° C. to 50° C. within 8 minutes, preferably from 130° C. to 70° C. within 3 minutes or shorter. After the old reagent has been replaced by new reagent, the heating platform should be capable of bringing the surface temperature from 50° C. to 150° C. within 8 minutes, preferably from 70° C. to 130° C. within 3 minutes or shorter.

The means of heating include radiant heat, electrical heating coils, circulating hot liquid or air, microwaves or other electromagnetic radiation or Peltier elements.

The solution can be exchanged in one of several ways. The slides can be turned to a vertical position to simply allow gravitational forces to pull the reagent off. Alternatively, the reagent can be blown off using compressed air. This may be done while the slide is in either a horizontal or a vertical position. No wash is needed during the exchange of the target retrieval solution.

In one embodiment, the target retrieval solution is replaced one or more times during heating. Replacing the target retrieval solution may e.g. be done between 0 and 10 times during the procedure.

One important property of this procedure is that during exchange of reagents when the temperature has been lowered as described above but before the old reagent is removed, the slide can enter a waiting phase. The waiting phase can be anything between 1 minute and 10 minutes or even longer. This introduces a great flexibility into an automated procedure, in relation to other procedures that may be ongoing in the instrument at the same time as the target retrieval procedure. However, once the reagent has been removed the new reagent should be added quickly, i.e. within 30 seconds, preferably within 15 seconds or more preferably 5 seconds.

In one embodiment of the invention, the temperature is achieved by heating the slide from below, thus the target retrieval solution is not in direct contact with the heating element. The highest temperature is achieved on the slide-surface where the tissue/cell sample is located. Preferably, the target retrieval is applied at ambient temperature, to avoid drying out the tissue, and the temperature is raised up to 100-150° C. within about 10 minutes, preferably within about 5 minutes, more preferably within about 3 minutes.

Cooling is performed in one of three methods: passive cooling on the heating element, active cooling on the heating element or passive cooling without contact with the heating element. In all cases the slides should be cooled to below 100° C., preferably below 60° C. while covered with the target retrieval solution. Preferably, the cooling is an active process, where the temperature is lowered to between ambient and 90° C. in about 10 minutes, more preferably to between ambient and 70° C. in about 5 minutes or even more preferably in about 3 minutes.

After cooling, the slide is washed with water, an aqueous washing buffer, ethanol or any other suitable solvent capable of mixing with the target retrieval solution. This washing step may be performed at ambient or above ambient temperature.

Enough target retrieval solution should be applied to cover the tissue, preferably between 1 and 2 ml dependent on the sample size, for example 1.2 ml, 1.3 ml or 1.5 ml for each application.

The total heating may vary with the target that is going to be stained, however heating times between about 5 and about 40 minutes are preferred.

As described above, there is an increasing demand for automation of immunohistochemistry procedures to reduce the amount of manual labor that is involved. This is driven by a desire to reduce the human errors as well as a lack of qualified laboratory personnel. With an increase in the amount of IHC-slides that are stained each year of approximately 20%, and at best a constant number of qualified persons to perform the staining, the need for automation of the processes presses on.

While conventional HIAR can be performed in pure water, the addition of further reagents to the target retrieval solution accelerates the hydrolysis reaction. This is also the case in the present invention.

The further reagents can be divided into 4 categories:
Bond-breakers that degrade the bonds formed by formaldehyde. This could be nucleophiles, Lewis acids or enzymes.
Protecting groups that react reversibly with the amino-groups that are liberated during target retrieval and prevent them from reacting with the fixative again.
Scavengers that react irreversibly with the fixative.
Chelators to remove divalent cations that stabilize the poly-oxy-methylene polymers.

These reagents can be used alone or in combination taking into consideration any possible reactions between reagents.

Nucleophiles may attack the bonds formed by formaldehyde and thereby increase the rate of degradation. Examples of such nucleophiles comprise ammonia, primary amines i.e. amines with one linear, branched or cyclic alkyl chain containing 0, 1 or multiple double or triple bonds and 0, 1 or multiple heteroatoms, such as oxygen, sulphur, nitrogen or others, or secondary alkylamines, i.e. amines with two linear, branched or cyclic alkyl chains of different or same length, each containing 0, 1 or multiple double or triple bonds and 0, 1 or multiple heteroatoms, such as oxygen, sulphur, nitrogen or others, or tertiary amines, i.e. amines with three linear, branched or cyclic alkyl chains of different or same length, each containing 0, 1 or multiple double or triple bonds and 0, 1 or multiple heteroatoms, such as oxygen, sulphur, nitrogen or others. Other examples of nucleophiles comprise hydrazines, halogenides or water. Examples of specific reagents that are included in the above description are tris(hydroxymethyl)aminomethane (TRIS), ethanolamin, hydrazine, ethylenediamine, diaminocyclohexane, hydrazine ethanol, piperidine, morpholine, tetrabutylammonium fluoride or others.

Another class of reagents is Lewis acids that due to their electron-deficiency react with electron-rich atoms and thereby weaken bonds to other atoms. Examples of Lewis acids comprise metal ions such as iron (III) chloride, aluminium chloride, magnesium chloride or other electron-deficient compounds such as toluenesulfonic acid, boric acid, boron trifluoride, tartaric acid or others.

Reagents that react with the liberated fixative will prevent it from reacting again. Examples of this comprise Purpald or Dimedone that are used to determine formaldehyde concentrations because they form very stable products that can be measured.

Alternatively, a reagent that reacts in a reversible way with the free amino-groups of the proteins thus protecting them from reaction with the available formaldehyde can be used for target retrieval. Citraconic anhydride (CCA) reacts in such a way.

Furthermore, there are indications that divalent cations form complexes with the poly-oxy-methylene polymers and conventional target retrieval buffers often contain chelators such as EDTA to remove these. Examples of chelators comprise EDTA, EGTA, EGTA/AM, BAPTA, BAPTA/AM, MAPTAM, TPEN, citrate or ionophores such as ionomycin or calcimycin.

EDTA and citrate are good for use in the target retrieval solution since they effectively form complexes with Ca2+, which is a divalent cation that is present in abundance in biological tissue or cell samples.

In addition to the reagents described above, a reagent for controlling the pH of the solution is often included in the HIAR-solution. pH can have a profound influence on the efficiency of target retrieval. Reagents for controlling the pH of the solution can be chosen from a wide range of buffers such as TRIS, citrate, phosphate, glycine or Good buffers, such as BES, BICINE, CAPS, EPPS, HEPES, MES, MOPS, PIPES, TAPS, TES or TRICINE.

The reagents may be chosen from, but are not limited to the examples presented above.

TRIS and citrate are good buffers for use in the target retrieval solution, since they have a good buffer-effect in the pH-ranges relevant for target retrieval and furthermore they have no negative effect on the biological samples.

EXAMPLES

General Procedures

Methods like deparaffinating, aqueous target retrieval, horizontal target retrieval and immunovisualisation, as used in the examples are hereby described in general. In the present case all procedures are performed manually except the immunovisualisation. The tissue on the slide is kept from drying out in every procedure.

General Deparaffination. Formalin Fixated Paraffin Embedded (FFPE) Tissue Mounted on Glass Slides are Deparaffinated in Xylene and Rehydrated in Ethanol.

In the procedure of deparaffinating sections of FFPE tissue on slides, the slides are manually transferred in a glass cradle as following in 200 ml jars; 2×5 minutes in xylene, 2×3 minutes in 96% ethanol, 2×3 minutes in 70% ethanol and minimum 1×5 minutes in TBS pH 7.6.

General Aqueous Target Retrieval. Heat Induced Epitope Retrieval (HIER) on Deparaffinated FFPE Tissue on Slides in 95-99° C. Target Retrieval Buffer.

A metal-jar with lid, containing 400 ml target retrieval buffer (ex. TRIS EDTA pH 9 or citrate pH 6) is placed in a 95-99° C. water bath, and the buffer is pre-heated to 95-99° C. The deparaffinated tissues on slides are transferred in a glass cradle to the 400 ml buffer in the jar. The target retrieval process proceeds for 20 or 40 minutes at 95-99° C. followed by a cooling period of 20 minutes in the jar of target retrieval buffer without the lid at room temperature. The slides are transferred in the glass cradle and placed in 200 ml TBS (TRIS-buffered saline) for at least 5 minutes.

General Horizontal Target Retrieval. Target Retrieval on Deparaffinated FFPE Tissue Slides Horizontal at Above 100° C.

A plate of aluminum (14 cm×14 cm×1.5 cm) is placed on the top of a heating device, which is controlled by a digital thermometer and heated above 100° C. The heating arrangement is placed in a shelter to minimize the airflow and the temperature is measured directly on the top of the plate by a separate unit.

The slide is taken from the TBS buffer and dried with a piece of paper avoiding the tissue, and approximate 1-2 mL of the horizontal target retrieval buffer is placed on the slide while making sure the tissue is completely covered, where after the slide with buffer is placed horizontally on the hot plate. Care is taken that the horizontal target retrieval buffer does not run off the slide to ensure that the tissue is protected from drying during heating.

It is possible to renew or change the horizontal target retrieval buffer on the slide by simply lifting the slides off the hot plate, holding the slide vertically over a waste container to let the buffer run off. Subsequently, the slide is covered with fresh unused horizontal target retrieval buffer, and placed on the hot plate again if needed. This can be repeated if needed.

To finish the horizontal target retrieval process, the buffer is allowed to run off the slide, and the slide is transferred into a jar of Milli Q water and thereafter washed by spraying with water from a bottle and finally transferred to a jar of TBS pH 7.6.

General Horizontal Target Retrieval Buffer. 10× Concentrated Buffer for Use in the Horizontal Target Retrieval Buffer.

In general two 10× concentrated buffers are made for use in preparing the horizontal target retrieval buffer as mentioned in the examples. They are made as following; 1) TE pH 9; 0.1M TRIS (Tris(hydroxymethyl)aminomethane), 10 mM EDTA (ethylenediaminetetraacetic acid), 2Na, $2H_2O$ pH 9.2) citrate pH 6.1; 2.5 mM citrate, 0.1% surfactant (alkylphenylpolyethyleneglycol), 0.01% Bronidox L pH 6.1.

General Immunovisualisation. Using Autostainer® (Dako) to Perform Immunostaining on Deparaffinated and Target Retrievaled FFPE Tissue.

The slide is placed in the AutoStainer® and immunovisualisation is performed as following; rinse in TBST (TRIS-buffered saline containing Tween), 5 minutes incubation in Peroxidase-Blocking solution (Dako, S2023), rinse in TBST, 30 minutes incubation in primary antibody, rinse in TBST, 30 minutes incubation in En Vision+ HRP anti mouse/rabbit visualization reagent (Dako, K5007), double rinse in TBST, 3 minutes incubation in DAB+(Dako, K5007), rinse in TBST, 5 minutes incubation in Haematoxylin (Dako, S3301), rinse in water, 5 minutes incubation in TBST, rinse in TBST. Finally, the slide is transferred into a jar of tap water.

After immunovisualisation, the tissue is dehydrated through jars containing increasing percent of ethanol in water, finished in xylene and permanently mounted using a few drops of tissue mount (Sakura, 1467) and a coverslip. After a period of drying, the slide is examined under a light microscope.

Example 1

Horizontal Target Retrieval Using Reagent Containing 30%, 50% or 70% Glycerol

Three different horizontal target retrieval buffers are made; 1) 30% glycerol (anhydrous), 60% Milli Q water, 10% TE pH 9, 2) 50% glycerol (anhydrous), 40% Milli Q water, 10% TE pH 9, 3) 70% glycerol (anhydrous), 20% Milli Q water, 10% TE pH 9.

Using Mamma Carcinoma tissue, slides are deparaffinated and retrieved horizontally as well as using the aqueous target retrieval as described in general procedures above. The horizontal target retrieval is performed at 130° C. measured on the hot plate. Furthermore, the reagent is changed every 5 minutes for totally 10 minutes (2×5 minutes) or 15 minutes (3×5 minutes). All three horizontal target retrieval buffers are tested. The aqueous target retrieval, which is made for comparison with the horizontal target retrieval slides, is performed in S2368 for 20 minutes.

Performing immunovisualisation, all tissue are stained as described in the general procedure, using Mouse anti-human ERα (Dako, M7047) diluted 1:35 (diluent, Dako, S2022) as primary antibody.

The horizontal target retrieval buffers containing 50 and 70% glycerol gave a specific ERα-staining of an intensity that is comparable to the aqueous target retrieval. The target retrieval buffer containing 30% glycerol gave slightly inferior staining.

There was insignificant evaporation of the target retrieval solution in all cases and none of the samples dried out during the procedure.

Example 2

Horizontal Target Retrieval with or without Buffer in the Reagent

Three different horizontal target retrieval reagents are made; 1) 50% glycerol, 50% Milli Q water. 2) 50% glycerol, 40% Milli Q water, 10% TE pH 9. 3) 50% glycerol, 40% Milli Q water, 10% citrate pH 6.1.

Using the tissue mentioned in table 1, slides are deparaffinated and retrieved horizontally as well as using the aqueous target retrieval as described in general procedures. The horizontal target retrieval is performed at 125° C. measured on the hot plate. Furthermore, the reagent is changed every 5 minutes for 10 minutes in total (2×5 minutes) regarding anti CD21 (Dako M0784) or 15 minutes (3×5 minutes) regarding anti ERα. The three horizontal target retrieval reagents are tested with both antibodies. The aqueous target retrieval recommended for each antibody is performed in the buffer mentioned in table 1 for 20 minutes.

TABLE 1

Tissue, antibody dilution and aqueous TR used for each antibody.

| Anti body Mouse anti-Human | Dilution | Tissue | Aqueous target retrieval |
|---|---|---|---|
| ERα | 1:35 | Mamma carcinoma | S2368 |
| CD21 | 1:50 | Tonsil | S1700 |

Performing immunovisualisation, all tissues are stained as described in the general procedure. Primary antibodies are used in the specific dilutions mentioned in table 1.

For both antibodies tested horizontal target retrieval reagent 1) lead to insufficient staining. Some ERα-staining was observed, however the intensity was too low, and in areas of the tissue where the aqueous target retrieval gave weak but distinct staining horizontal target retrieval reagent 1) gave no staining. Staining with CD21 was completely negative. Reagent 2) also gave a completely negative stain for CD21, however the ERα-staining was comparable to the staining achieved with the aqueous target retrieval. Horizontal target retrieval reagent 3) lead to a staining that was comparable to the aqueous target retrieval for both antibodies.

This example illustrates the importance of pH-control in the target retrieval reagent. As exemplified by CD21, a difference in the pH of the target retrieval reagent can mean the difference between a good staining and a completely negative staining.

Example 3

Renewing the Horizontal Target Retrieval Buffer

A horizontal target retrieval buffer is made; 50% glycerol, 40% Milli Q water, 10% TE pH 9. Using Mamma Carcinoma tissue, slides are deparaffinated and retrieved horizontally as well as using the aqueous target retrieval as described in general procedures. The horizontal target retrieval is performed at 125° C. measured on the hot plate.

The horizontal target retrieval is performed by adding the reagent and heating the slides for 10 or 15 minutes. For half of the slides, the same reagent remains on for the entire heating period. For the other half of the slides the buffer is changed every 5 minutes for totally 10 minutes (2×5 minutes) or 15 minutes (3×5 minutes). The aqueous target retrieval is performed in S2368 for 20 minutes.

Performing immunovisualisation, all tissue are stained as described in the general procedure, using Mouse anti-human ERα diluted 1:35 as primary antibody.

The slides where the same reagent remains on for 10 minutes show weak or negative staining. Increasing the time to 15 minutes, also increases the staining intensity, however the reagents of this example show poorer staining compared to the aqueous target retrieval. The slides where the buffer is renewed every 5 minutes all show acceptable staining and the slides that have been subjected to 3×5 minutes horizontal target retrieval show a staining of the same intensity as the aqueous target retrieval.

Example 4

Horizontal Target Retrieval Using TE pH 9 as Buffer in the Horizontal Target Retrieval Reagent Five different antibodies are tested; Mouse anti-Human PR (Dako M3569), BCL2 (Dako M0887), Cytokeratin 5/6 (Dako M7237), CD20cy (Dako M0755) and Rabbit anti-Human HER2 (Dako, K5204).

A horizontal target retrieval buffer with TE pH 9 is made; 50% glycerol, 40% Milli Q water, 10% TE pH 9.

Using tissue mentioned in table 2, slides are deparaffinated and retrieved horizontally as well as using the aqueous target retrieval as described in general procedures. The horizontal target retrieval is performed at 125° C. measured on the hot plate. Furthermore, the reagent is changed every 5 minutes for totally 10 minutes (2×5 minutes) or 15 minutes (3×5 minutes). The aqueous target retrieval is performed in the buffer mentioned in table 2 for 20 minutes, except the tissue used with the HER2 antibody, which is retrieved for 40 minutes.

TABLE 2

Tissue, antibody dilution and aqueous target retrieval used for each antibody.

| Anti body Mouse anti-Human | Dilution | Tissue | Aqueous target retrieval |
|---|---|---|---|
| PR | 1:20 | Mamma carcinoma | Citrate pH 6 |
| BCL2 | 1:100 | Large Multi | TRIS EDTA pH 9 |
| Cytokeratin 5/6 | 1:100 | Large Multi | TRIS EDTA pH 9 |
| CD20cy | 1:400 | Large Multi | TRIS EDTA pH 9 |
| HER2 (rabbit) | RTU | Mamma carcinoma | Herceptest ER buffer |

Performing immunovisualisation, all of the tissues are stained as described in the general procedure except regarding the HER2 antibody which is immunostained using the Herceptest reagents as specified in the kit. Primary antibodies are used in the specific dilution mentioned in table 2.

For all antibodies we obtained specific staining of an intensity that was comparable to staining obtained with the aqueous target retrieval. For PR, HER2 and CD20cy, the best results were obtained with 2×5 minutes and for BCL2 and Cytokeratin 5/6 3×5 minutes was optimal.

Example 5

Horizontal Target Retrieval Using Citrate pH 6.1 as Buffer in the Horizontal Target Retrieval Buffer Two different antibodies are tested; Mouse anti-Human CD21 and Epithelial Antigen (Dako M0804).

A horizontal target retrieval buffer with citrate pH 6.1 is made; 50% glycerol, 40% Milli Q water, 10% citrate pH 6.1.

Using tissue mentioned in table 3, slides are deparaffinated and retrieved horizontally as well as using the aqueous target retrieval as described in general procedures. The horizontal target retrieval is performed at 125° C. measured on the hot plate. Furthermore, the reagent is changed every 5 minutes for totally 10 minutes (2×5 minutes) or 15 minutes (3×5 minutes). The aqueous target retrieval is performed in the buffer mentioned in table 3 for 20 minutes.

TABLE 3

Tissue, antibody dilution and aqueous TR used for each antibody.

| Anti body Mouse anti-Human | Dilution | Tissue | Aqueous target retrieval |
|---|---|---|---|
| CD21 | 1:50 | Tonsil | Citrate pH 6 |
| Epithelial Antigen | 1:400 | Large Multi | Citrate pH 6 |

Performing immunovisualisation, all of the tissues are stained as described in the general procedure. Primary antibodies are used in the specific dilution mentioned in table 3.

For both antibodies we obtained specific staining of an intensity that was comparable to staining obtained with the aqueous target retrieval. For CD21 the best result was obtained with 2×5 minutes and for Epithelial Antigen 3×5 minutes was optimal.

Example 6

Horizontal Target Retrieval Using Citrate pH 6.1 and TE pH 9 as Buffers in a Mixture of Propylene Glycol and Ethylene Glycol for the Horizontal Target Retrieval Solution Two target retrieval solutions are made; 55% propylene glycol, 25% ethylene glycol, 10% Milli Q water, 10% citrate pH 6.1 or TE pH 9. Using Mamma Carcinoma tissue, slides are deparaffinated and retrieved horizontally as well as using the aqueous target retrieval as described in general procedures. The horizontal target retrieval is performed in an oven at 120° C. as measured in the reagent.

The horizontal target retrieval is performed by adding the solution of this example to the slide and placing the slides in the pre-heated oven. The slides are heated for 20 or 40 minutes. Then target retrieval solution is exchanged when needed. After the horizontal target retrieval is complete, the slides are rinsed under 99.9% ethanol followed by submersion in 2 times 96% ethanol and 2 times 70% ethanol and ending in TBS. The aqueous target retrieval is performed in S2368 for 20 minutes.

Performing immunovisualisation, all tissue are stained as described in the general procedure, using Mouse anti-human ERα diluted 1:35 as primary antibody.

The invention claimed is:

1. A method for enhancing immunoreactivity of a tissue or cell sample fixed in a fixing medium, comprising:
    providing a carrier in a horizontal position, said carrier having thereon a tissue or cell sample, said tissue or cell sample being on top of the carrier;
    applying an amount of a buffered target retrieval solution to the tissue or cell sample side of the carrier to cover the tissue or cell sample without submerging the carrier, wherein the target retrieval solution remains otherwise exposed to the environment; and
    heating the tissue or cell sample and the target retrieval solution at a temperature above 100° C.

2. The method according to claim 1, wherein more than one tissue or cell sample is placed on top of the carrier, and where in the amount of buffered target retrieval solution applied covers the more than one tissue or cell sample.

3. The method according to claim 1, wherein the carrier is a glass slide, a slide made of a polymer material, or a membrane.

4. The method according to claim 1, wherein the buffered target retrieval solution does not evaporate to a measurable degree when heated at a temperature between 100° C. and 150° C.

5. The method according to claim 1, wherein the target retrieval solution is heated to a temperature between 100° C. and 200° C.

6. The method according to claim 1, wherein the target retrieval solution is heated to a temperature between 100° C. and 150° C.

7. The method according to claim 1, wherein the target retrieval solution is heated to a temperature between 105° C. and 130° C.

8. The method according to claim 1, wherein the target retrieval solution comprises a solvent having a boiling point significantly higher than the boiling point of water.

9. The method according to claim 1, wherein the target retrieval solution comprises a solvent having a boiling point higher than the boiling point of water and lower than 199° C.

10. The method according to claim 1, wherein a solvent of the target retrieval solution is selected from the group consisting of alcohols, glycols, ketones, esters, amides, nitriles, and mixtures thereof.

11. The method according to claim 10, wherein the solvent is glycerol.

12. The method according to claim 10, wherein the solvent is selected from propylene glycol, ethylene glycol, and mixtures thereof.

13. The method according to claim 1, wherein the target retrieval solution further comprises one or more reagents capable of breaking bonds formed during fixation of the biological sample.

14. The method according to claim 1, wherein the target retrieval solution comprises more than 25% (v/v) of a solvent.

15. The method according to claim 1, wherein the target retrieval solution comprises between 40% (v/v) and 80% (v/v) of a solvent.

16. The method according to claim 1, wherein the target retrieval solution comprises between 45% (v/v) and 75% of a solvent.

17. The method according to claim 1, wherein the target retrieval solution comprises about 50% (v/v) of a solvent.

18. The method according to claim 1, wherein the fixing medium is selected from formaldehyde, Bouins solution, Periodate/Lysine/Paraformaldehyde, paraformaldehyde, Boonfix I, Boonfix II, Myrsky's fixative, glutaraldehyde, a zinc formalin, an aldehyde, and mixtures thereof.

19. The method according to claim 1, further comprising automation of one or more steps.

20. The method according to claim 1, further comprising cooling the carrier and the target retrieval solution after heating the tissue or cell sample and the target retrieval solution.

21. The method according to claim 1, further comprising removing the target retrieval solution from the surface of the carrier after (i) heating the tissue or cell sample and the target retrieval solution and/or (ii) cooling the carrier and the target retrieval solution.

22. The method according to claim 21, wherein the target retrieval solution is removed from the surface of the carrier using a further solvent capable of mixing with the target retrieval solution.

23. The method according to claim 22, wherein the further solvent is selected from water, an aqueous washing buffer, and ethanol.

24. The method according to claim 21, wherein the removing of the target retrieval is performed at ambient or above ambient temperature.

25. The method according to claim 1, further comprising renewing or replacing the target retrieval solution one or more times during the heating of the tissue or cell sample and the target retrieval solution.

26. The method according to claim 1, further comprising staining the tissue or cell sample with a probe.

27. A method for enhancing the immunoreactivity of a tissue or cell sample fixed in a fixing medium, wherein the method comprises applying an amount of a target retrieval solution to the tissue or cell sample to cover the tissue or cell sample without submerging the carrier; and wherein the target retrieval solution comprises glycerol, water, and one or more further reagents selected from a nucleophile, a buffer, a chelator, and a detergent.

* * * * *

UNITED STATES PATENT AND TRADEMARK OFFICE
CERTIFICATE OF CORRECTION

PATENT NO.        : 8,465,944 B2
APPLICATION NO.   : 12/526323
DATED             : June 18, 2013
INVENTOR(S)       : Nanna K. Christensen It is certified that error appears in the above-identified patent and that said Letters Patent is hereby corrected as shown below:

In the Claims:

In claim 2, col. 20, lines 15-16, "where in" should read --wherein--.

Signed and Sealed this
Third Day of September, 2013

Teresa Stanek Rea
*Acting Director of the United States Patent and Trademark Office*